US007445776B2

(12) United States Patent
Hanley, Jr. et al.

(10) Patent No.: US 7,445,776 B2
(45) Date of Patent: *Nov. 4, 2008

(54) METHOD FOR PRODUCING HUMAN INTERVERTEBRAL DISC CELLS FOR IMPLANTATION

(75) Inventors: Edward Nathaniel Hanley, Jr., Charlotte, NC (US); Helen Elizabeth Gruber, Charlotte, NC (US)

(73) Assignee: Charlotte-Mecklenburg Hospital Authority, Charlotte, NC (US)

( * ) Notice: Subject to any disclaimer, the term of this patent is extended or adjusted under 35 U.S.C. 154(b) by 241 days.

This patent is subject to a terminal disclaimer.

(21) Appl. No.: 11/151,141

(22) Filed: Jun. 13, 2005

(65) Prior Publication Data

US 2005/0232903 A1    Oct. 20, 2005

Related U.S. Application Data

(63) Continuation of application No. 09/560,288, filed on Apr. 27, 2000, now Pat. No. 7,101,545, which is a continuation-in-part of application No. 08/979,674, filed on Nov. 26, 1997, now Pat. No. 6,080,579.

(51) Int. Cl.
*A61K 35/32* (2006.01)
*A61K 35/30* (2006.01)
*C12N 5/08* (2006.01)

(52) U.S. Cl. .................. 424/93.7; 435/368; 435/379; 435/382

(58) Field of Classification Search ............... None
See application file for complete search history.

(56) References Cited

U.S. PATENT DOCUMENTS

| | | | |
|---|---|---|---|
| 4,485,097 A | 11/1984 | Bell | |
| 5,032,508 A | 7/1991 | Naughton et al. | |
| 5,155,034 A | 10/1992 | Wolf et al. | |
| 5,256,418 A | 10/1993 | Kemp et al. | |
| 5,266,476 A | 11/1993 | Sussman et al. | |
| 5,422,340 A | 6/1995 | Ammann et al. | |
| 5,496,722 A | 3/1996 | Goodwin et al. | |
| 5,585,116 A | 12/1996 | Boniface et al. | |
| 5,964,807 A * | 10/1999 | Gan et al. | 424/423 |
| 6,080,579 A | 6/2000 | Hanley, Jr. et al. | |
| 6,340,369 B1 | 1/2002 | Ferree | |
| 7,101,545 B1 * | 9/2006 | Hanley et al. | 424/93.7 |

OTHER PUBLICATIONS

Martin, in Tissue Culture, Methods and Applications, Ed., P.F. Kruse, Jr., and M.K. Patterson, Jr., Academic Press, NY, Chapter 1, pp. 39-43, 1973.
Malemud et al., Matrix, 12:427-438, 1992.
Aulthouse et al., In Vitro Cell. Develop. Biol., 25:659-668, 1989.
Paul D. Benya, et al., Dedifferentiated Chondrocytes Reexpress The Differentiated Collagen Phenotype When Cultured In Agarose Gels, *Cell*, vol. 30, Aug. 1982, pp. 215-224.
Jinfeng Guo, et al., Culture And Growth Characteristics Of Chond4rocytes Encapsulated In Alginate Beads, *Connective Tissue Research*, vol. 19, 1989, pp. 277-297.
J. Paul Thompson, et al., Stimulation Of Mature Canine Intervertebral Disc By Growth Factors, *Spine*, vol. 16, No. 2, 1991, pp. 256-260.
Brian A. Maldonado, et al., Initial Characterization Of The Metabolism Of Intervertebral Disc Cells Encapsulated In Microspheres, *Journal Of Orthopaedic Research*, vol. 10, 1992, pp. 677-690.
J. Bonaventure, et al., Reexpression Of Cartilage-Specific Genes By Dedifferentiated Human Articular Chondrocytes Cultured In Alginate Beads, *Experimental Cell Research*, vol. 212, 1994, pp. 97-104.
Mary K. Chelberg, et al., Identification Of Heterogeneous Cell Populations In Normal Human Intervertebral Disc, *J. Anat.*, vol. 186, Accepted Jul. 6, 1994, pp. 43-53.
Steven L. Frick, et al., Lumbar Intervertebral Disc Transfer—A Canine Study, *Spine*, vol. 19, No. 16, Aug. 15, 1994, pp. 1826-1835.
Akitomo Katsuura, et al., Experimental Study Of Intervertebral Disc Allografting In The Dog, Spine, *Spine*, vol. 19, No. 21, Nov. 1, 1994, pp. 2426-2432.
Job L. C. van Susante, et al., Culture Of Chondrocytes In Alginate And Collagen Carrier Gels, *Acta Orthop Scand*, vol. 66, No. 6, 1995, pp. 549-556.

(Continued)

Primary Examiner—Robert C Hayes
(74) Attorney, Agent, or Firm—Alston & Bird LLP

(57) ABSTRACT

There is provided a method for growing human intervertebral cells. Disc tissue is surgically removed from a normal disc of a patient, the cells expanded by feeding with a cell stimulant such as a growth factor, or a cytokine or a bioactive agent to form monolayer primary cell cultures on a plastic mesh such as a nylon mesh. In the case of a growth factor, fetal bovine serum is preferred as it improves cell proliferation and production of appropriate extracellular matrix components. In another aspect of this invention, the monolayer primary cell cultures are seeded in alginate or agarose and fed again with the cell stimulant until three-dimensional cell cultures are formed. The cells are recovered from the alginate or agarose or from monolayer cultures. Re-implantation is carried out using bioresorbable carriers or cell suspensions.

9 Claims, 7 Drawing Sheets

OTHER PUBLICATIONS

C. Frondoza, et al., Human Chondrocytes Proliferate And Produce Matrix Components In Microcarrier Suspension Culture, *Biomaterials*, vol. 17, 1996, pp. 879-888.

Hiromi Matsuzaki, et al., Allografting Intervertebral Discs In Dogs—A Possible Clinical Application, *Spine*, vol. 21, No. 2, Jan. 15, 1996, pp. 178-183.

Kjell Olmarker, et al., Ultrastructural Changes In Spinal Nerve Roots Induced By Autologous Nucleus Pulposus, *Spine*, vol. 21, No. 4, Feb. 15, 1996, pp. 411-414.

*Transforming Growth Factor-β1 (TGF-β) Regulates Proliferation and Proteoglycan Gene Expression in Diseased Human Intervertebral Disc Cells*, H. E. Gruber et al., J. Bone Mineral Res: 11 (suppl. 1): S300, 1996.

Wang et al. in Chemistry and Biology of Mineralized Tissues; ed. H. Slavkin and P. Price, Elsevier Science Publishers B. V., pp. 351-359, 1992.

Gruber et al., Exp. Cell Research, 235: 13-21, 1997.

Maurer, in Animal Cell Culture, A Practical Approach, ed. RI Freshney, IRL Press, pp. 13-31, and 150-151, 1987.

Osada et al. Journal of Orthopaedic Research, 14:690-699, 1996.

Luk et al., Clin. Orthopaed. Rel. Res., 337:13-26, 1997.

Guilak et al., Spine, 24:2475-2483, 1999.

Aigner et al., Calcif. Tiss. Int., 63:263-268, 1998.

\* cited by examiner

METHOD FOR PRODUCING HUMAN INTERVERTEBRAL DISC CELLS FOR IMPLANTATION

RELATED U.S. APPLICATIONS

This application is a continuation of and claims priority from U.S. patent application Ser. No. 09/560,288, filed Apr. 27, 2000 now U.S. Pat. No. 7,101,545, issued Sep. 6,2006, which is a continuation-in-part of and claims priority from U.S. patent application Ser. No. 08/979,674, filed Nov. 26, 1997, now U.S. Pat. No. 6,080,579, issued Jun. 27,2000, which is incorporated herein by reference in its entirety.

BACKGROUND OF THE INVENTION

This invention relates to a method for producing human intervertebral disc cells. More particularity, this invention relates to methods for growing intervertebral cells in monolayers cultures followed by three-dimensional growth of cells.

In spite of the large health care costs associated with degenerative disc disease, the cell biology of the human intervertebral disc cell has been neglected compared to the knowledge available on chondrocytes or bone cell populations. Recent studies have presented data on the formation and turnover of matrix in situ in the human disc. Antoniou, J., Steffen, T., Nelson, F., Winterbottom, N., Hollander, A. P., Poole, R. A., Aebi, M., Alini, M., "The human lumbar intervertebral disc-Evidence for changes in the biosynthesis and denaturation of the extra cellular matrix with growth, maturation, ageing, and degeneration," *J. Clin. Invest.* 98, 996-1003 (1996). Growth of the young disc showed active matrix formation and denaturation of Type II collagen; aging and maturation were associated with decreased matrix synthesis and reduced denaturation of Type II collagen. Degenerative stages showed decreased aggrecan and Type II procollagen formation and increased Type II denaturation and Type I collagen synthesis. Successful isolation and in vitro growth of disc cells under experimental conditions can be a valuable tool for clarification of the cellular mechanisms involved in these observed matrix changes.

Studies of human disc cells cultured in alginate beads have provided evidence that more than one distinctive cell population resides in the disc. Chelberg, M. K., Banks, G. M., Geiger, D. F., Oegema, T. R., "Identification of heterogeneous cell populations in normal human intervertebral disc," *J Anat,* 186, 43-53 (1995). Others have used the alginate bead technique to study canine disc cells in culture. Maldonado, B. A., Oegema, T. R., "Initial characterization of the metabolism of intervertebral disc cells encapsulated in microspheres," *J Orthopaedic Res,* 10, 677-690 (1992). Cells from the rat disc have been grown in monolayer culture. Ichimura, K., Tsuji, H., Matsui, H., Makiyama, N., Cell culture of the intervertebral disc of rats: Factors influencing culture, proteoglycan, collagen, and deoxyribonucleic acid synthesis," *J Spinal Disorders,* 4, 428-436 (1991).

Three-dimensional cell culture is a preferred culture method for chondrocytes, a cell type similar to at least some members of the disc cell population, and is known to de-differentiate in monolayer culture and reexpress a characteristic Type II collagen extracellular matrix production when placed in agarose culture. Benya, P. D., Shaffer, J. D., "Dedifferentiated chondrocytes reexpress the differentiated collagen phenotype when cultures in agarose gels," *Cell,* 30, 215-224 (1982).

It is an object of the present invention to produce human intervertebral cells in monolayer explant cultures.

Another object of the present invention is to produce human intervertebral cells in a three-dimensional cultures.

SUMMARY OF THE INVENTION

The present invention provides methods for propagating human intervertebral disc cells in vitro and treating human intervertebral disc diseases using the in vitro expanded disc cells.

In accordance with a first aspect of this invention, intervertebral disc cells obtained from a human are cultured in vitro in the presence of a cell stimulant such as a growth factor, or a cytokine or a bioactive agent to form monolayer cultures. In the case of a growth factor, fetal bovine serum is preferred as it improves cell proliferation and production of appropriate extracellular matrix components. Preferably, an explant is first obtained from a human disc specimen, and cultured in cell culture media with a plastic mesh as an anchor. The cells in the monolayer culture are capable of continuously proliferating and passaging for generations.

In accordance with a second aspect of this invention, the monolayer primary cell cultures may be seeded into a carrier such as alginate, agarose, collagen, and the like, and cultured in the carrier to form a three-dimensional structure. Typically, cell culture media, and optionally, cell stimulants such as fetal bovine serum, growth factors and the like are added to the three-dimensional structure such that the cells further proliferate and re-express extracellular matrix materials.

In accordance with another aspect of the present invention, a method for treating intervertebral disc diseases in a human patient is provided by implanting the cultured human intervertebral disc cells of the present invention into the site to be treated. In one embodiment, healthy disc specimens are obtained from the patient to be treated. The disc cells are cultured and propagated in a monolayer culture and/or three-dimensional structure in accordance with the cell culture methods of this invention. Damaged disc tissue in the patient can be removed, and the cultured disc cells are implanted to the area where the damaged disc tissue has been removed. Typically, an implantation carrier, preferably a bioresorable carrier, is employed for purpose of implanting the cultured cells. The implantation can be performed by conventional surgical methods known in the art.

The method can be effective in treating various human intervertebral disc diseases such as idiopathic scoliosis, disc herniation, disc degeneration, and spinal stenosis.

BRIEF DESCRIPTION OF THE DRAWINGS

FIG. 7B,X485)

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Figure 1:
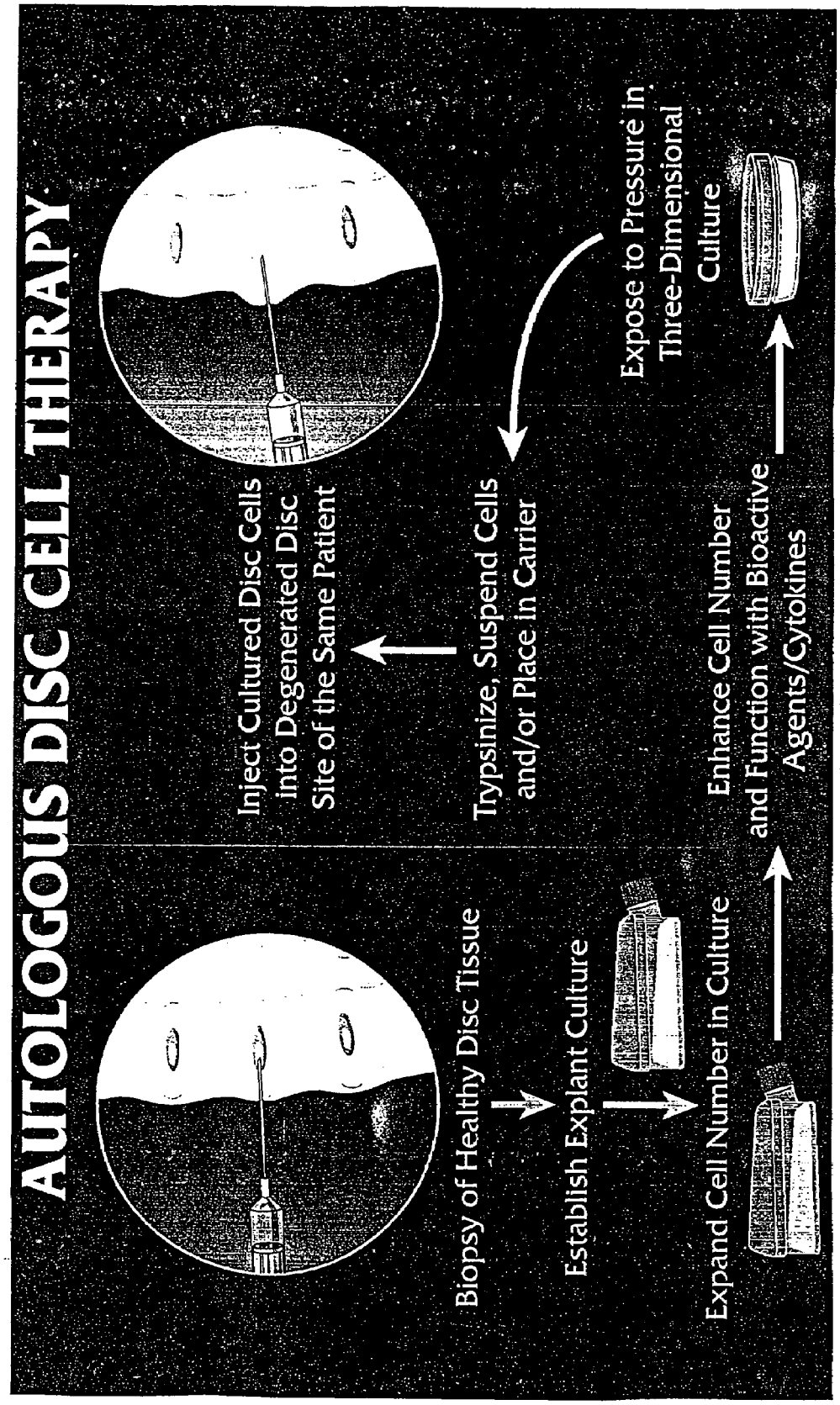
FIG. 1 is a schematic illustration of one embodiment of the method of treating disc disease of the present invention.

The present invention is directed to a method for producing human intervertebral cells which are intended for implantation into a patient. It is important that the cells implanted into the patient be grown from the patient's own cells. The present invention in one embodiment provides growing intervertebral cells by feeding with a cell stimulant or merely using an expanded number of cells from monolayer explant culture (primary culture). In another embodiment, this invention provides seeding cells from the primary culture into three-dimensional growth environments of alginate or agarose and continued feeding with cell culture media. As shown in FIG. 1, disc tissue is surgically removed from a normal disc of a patient, the cells expanded by feeding with a cell stimulant on a plastic mesh such as a nylon mesh, grown in a three-dimensional microenvironment with cell stimulants such as growth factors and bioactive agents to re-express phenotype, placed in a carrier material or injected as a cell suspension and inserted into a site with disc degeneration in that same patient.

Production of a Monolayer Culture (Primary Culture)

Disc tissue is derived from surgical disc procedures performed on individuals with idiopathic scoliosis, herniated disc, degenerative disc disease, recurrent disc herniation or spinal stenosis and the like. Healthy disc tissue may be obtained by any of the known surgical procedures and placed in a sterile medium and incubated with fungizone as a precaution against contamination. The healthy disc tissue is rinsed with phosphate buffered saline. Regions of annulus and nucleus are visually identified and representative pieces of annulus and nucleus are dissected. Those designated for culturing cells are further examined and any cartilaginous or vascular regions are carefully removed. The disc tissue to be cultured is minced into 1-2 mm square pieces, again rinsed with saline to remove clots or residual debris, placed into culture dishes and anchored by placement of a sterile nylon mesh over the minced explant. Use of the nylon mesh anchoring technique for explants not only simplifies the feeding of cultures by anchoring fragments and thus preventing loss of fragments during cell feeding, but also provides a substrate for cell outgrowth.

To the designated cells is added Minimal Essential Medium (MEM, Gibco) with Earle's salts, 1% L-glutamine, 1% non-essential amino acids, 1% penicillin-streptomycin and about 20% (v/v) of a cell stimulant, such as a growth factor, or a cytokine or a bioactive agent. Fetal calf serum and fetal bovine serum (Gibco, Grand Island, N.Y.) are preferred. Other cell stimulants include, for example, transforming growth factor beta (TGF-β), insulin-like growth factor I, insulin-like growth factor II, basic fibroblast growth factor, acidic fibroblast growth factor, platelet-derived growth factor, serum, insulin, human recombinant bone morphogenetic protein 2, Vitamin D, 1,25-dihydroxyvitamin D, and other forms of bone morphogenetic protein or ITS (insulin-transferrin-selenium). Serum may or may not be present during feeding with the cell stimulant. Cells may also be grown in the Hams medium with addition of previously mentioned agents.

The primary cultures are grown at a temperature of about 37° C. Normally, the primary cultures are grown at high humidity conditions under a blanket of $CO_2$. These cultures are fed with the cell stimulant every two days. When primary cultures show a confluent outgrowth of cells from the nylon mesh, the cultures are trypsinized. It has been found that cell viability may average 96% on a monolayer culture.

Three-Dimensional Cell Growth

Following trypsinization, cells established in monolayer primary cultures may be seeded into a carrier material such that the cells are dispersed and distributed in the carrier material forming a three-dimensional structure. Alternatively, frozen cells derived from the monolayer human intervertebral disc cell culture of the present invention can also be seeded. Any suitable carrier materials known in the art can be used. The carrier material should be selected such that the disc cells can proliferate and re-express extracellular matrix materials. Typically, a polymerizable material is used. Preferably, alginate, agarose, collagen, or a derivative or a mixture thereof is used as carrier material. Although not required, it is preferable that the carrier material is bioresorbable, i.e., when implanted in the body of a mammal, it is capable of being absorbed by tissues of the body. As used herein, "carrier material" also means compositions containing alginate, and/or agarose, and in addition, some other compatible components such as buffer ingredients, growth factors, cytokines, serum, and the like. Typically, after forming the three-dimensional structure, the dispersed cells are embedded in the three-dimensional structure. To culture the cells within the three-dimensional structure, cell culture medium including growth factors, buffering agents, and the like is fed to the cells. For example, the three-dimensional structure can be immersed in a suitable cell culture medium which is changed regularly. The medium should be in intimate contact with the three-dimensional structure such that the medium can penetrate the three-dimensional structure to supply sufficient nutrition to the embedded cells.

Thus, a three-dimensional human disc cell culture can be established containing human intervertebral disc cells embedded in a carrier material forming a three-dimensional structure. In accordance with the present invention, the human disc cells seeded in the three-dimensional structure are capable of proliferating and/or re-expressing extracellular matrix materials within the three-dimensional structure. Therefore, after being cultured for a period of time, the three-dimensional cell culture contains at least a portion of human intervertebral disc cells produced by cell proliferation within the three-dimensional structure.

In a typical procedure in accordance with the present invention, trypsinized monolayer cell cultures are assayed for cell viability and the required volume of cell suspension centrifuged and the medium aspirated off.

Regarding alginate, an alginate solution may be prepared by mixing a 1.2% solution of Keltone LV alginate (Kelco, San Diego, Calif.) in 0.9% physiological saline and then sterilized. An appropriate volume of the sterile alginate solution is added to attain the desired cell/alginate suspension.

The three-dimensional cell structures are grown in multi-well plates. Inserts are placed in the bottom of each well. One type of insert that may be used is a Costar Transwell Clear Insert (Costar, Cambridge, Mass.). The alginate/cell suspension is added to the insert.

After the alginate/cell suspension is in place, a polymerizing solution is added to the well. The polymerizing solution may be one having a divalent cation. A preferred polymerizing solution is $CaCl_2$. The alginate/cell suspension is incubated in the polymerizing solution for four minutes and the solution aspirated out. Wells were rinsed with MEM with 20% FBS. The rinsing volume is allowed to stand for one minute, aspirated off, and the wells filled with MEM and cell stimulant (as described above) and regularly fed. Methods for disc cell growth in alginate are a modification of the methods described in Maldonado, B. A., Oegema, T. R., "Initial characterization of the metabolism of intervertebral disc cells encapsulated in microspheres," *J Orthopaedic Res,* 10, 677-690 (1992) and Guo, J., Jourdian, G. W., MacCallum, D. K., "Culture and growth characteristics of chondrocytes encapsulated in alginate beads," *Conn Tiss Res* 19:227-297 (1989).

The cells can be recovered from alginate by rinsing with NaCl followed by addition of a dissolving buffer, incubated until the alginate is dissolved, centrifuged and rinsed again with NaCl. Cells can also be similarly recovered from agarose and other carrier types, as required. These cells, grown in this manner, may be implanted into the patient's disc as described below.

Method of Treating Human Disc Diseases

In accordance with another aspect of the present invention, the human intervertebral disc cells obtained according to the present invention are used in treating disc diseases in human patients. In particular, the method of this invention can be used to treat patients having an area in the disc that is defective, e.g., damaged or degenerated. For example, the method of the present invention can be used in treating human disc diseases such as idiopathic scoliosis, disc degeneration, disc herniation, spinal stenosis, and the like.

An embodiment of the method is outlined in FIG. 1. Both cells in monolayer cell cultures and those propagated in three-dimensional structures as described above can be used in treating human diseases in accordance with this invention. It is preferable that autologous disc cells propagated in vitro according to the cell culture methods of this invention are used. To this end, healthy disc specimens are obtained from the patient to be treated. Explants are isolated from the specimens and cultured as described above to provided monolayer cell cultures. Cells in the monolayer cell cultures can be frozen and stored until use, or used directly for implantation. Alternatively, cells from the monolayer cell cultures can be further cultured in a three-dimensional structure so that the cells further propagate and, optionally, re-express extracellular matrix materials. The cells propagated in the three-dimensional structure can be recovered from the three-dimensional structure, i.e., separated from the carrier in the three-dimensional structure.

Normally, the in vitro propagated human disc cells are loaded into an "implantation carrier." As used herein, the term "implantation carrier" means any materials or structures suitable as a transplantation carrier to facilitate the implantation, adhesion, migration, and survival and growth of the implanted cells. Implantation carriers are generally known in the art. For example, suitable implantation carrier can be in the form of a gel or a three-dimensional assembly formed from one or more biocompatible materials, e.g., alginate, collagen, agarose, dextran, chondroitin, polyethylene glycol, etc. Hydrogels are known in the art and typically cells embedded in hydrogels can be implanted by, e.g., injecting the cell-containing hydrogel into the desired area in the patient. Alternatively, a three-dimensional construct with cells embedded therein can be implanted to the desired area in the patient. For example, in vitro propagated human disc cells can be seeded within a three-dimensional construct similar to the encapsulation membranes or porous matrices disclosed in, e.g., U.S. Pat. Nos. 4,353,888, 4,487,758, and 4,902,295, all of which are incorporated herein by reference. Porous constructs can have an interconnected macroporous structure formed by one or more biocompatible materials which constitutes the skeleton of the structure. Growth factors and other signaling molecules can also be included in the hydrogel or construct for modifying cell adhesion, growth, or migration after implantation. Preferably, the biocompatible materials used in the implantation carrier is bioresorbable. Commercial products such as Gelfoam® from Pharmacia, and SeaPlaque or SeaPrep agarose from FMC Bioproducts, alginate from Kelco, DuraGen from Integra LifeSciences Corp., and Vitrogen 100® from Collagen Corporation can be used advantageously.

Normally, the three-dimensional structure used in propagating human disc cells as described above can be used as a three-dimensional construct for implantation purposes. Thus, after disc cells have proliferated and re-expressed extracellular matrix materials in the three-dimensional structure to a desired extent, the three-dimensional structure can be implanted directly to the desired area in the patient. To facilitate the implantation procedure, the three-dimensional structure can be converted into a desired shape or size before implantation by cutting or other techniques.

The implantation of in vitro propagated human disc cells, preferably in an implantation carrier, can be performed by any suitable procedures known in the art. For example, where debridement of the defect disc tissue is not required, the disc cells embedded in, e.g., an injectible hydrogel can be injected into the desired area of the intervertebral disc of the patient without invasive surgical procedures. However, very often, it is desirable to remove the diseased disc tissue before the implantation of the in vitro cultured disc cells. In that event, the diseased disc tissue can be surgically removed creating a cavity or void, and in vitro cultured human disc cells, preferably autologous disc cells, in an implantation carrier are implanted in the removed area.

Surgical techniques for removing diseased disc tissues and for surgically implanting a three-dimensional construct in human intervertebral discs are known in the art and can all be used in the present invention. For example, Wood and Hanley, *Opera. Tech. Ortho.* 1:23-28 (1991) (which is incorporated herein by reference) discloses a laminectomy technique for removing herniated lumbar disc. Percutaneous discectomy techniques are disclosed in, e.g., U.S. Pat. Nos. 4,545,374; 5,242,439; and RE 33,258, all of which are incorporated herein by reference. Various endoscopic/laparoscopic surgery instruments and techniques are described in, e.g., U.S. Pat. Nos. 5,195,541; 5,201,729; 5,620,458; and 5,980,504, all of which are incorporated herein by reference.

After the removal of the diseased disc tissue, the in vitro propagated cells in an implantation carrier are implanted to the target area needing treatment. Implantation can be performed following the surgical debridement procedure while the target area for treatment is exposed or accessible. Alternatively, implantation can also be performed separately by, e.g., percutaneous procedures via posterior approaches, or anterior or oblique techniques. The implantation can be conducted by standard transplantation techniques, as will be clear to an ordinarily skilled artisan.

Particularly, the size and shape of the three-dimensional construct to be implanted containing the in vitro propagated human disc cells should be adapted to the target area of implantation such that the pressure, volume, degree of disc distention, and the like in the area are appropriate after the implantation. It is important to ensure that the implanted construct is such that the nerve root in the area is not compressed excessively.

The number of cells to be implanted can vary with the size of the area to be treated. The cell density in the implantation carrier should be selected such that the cells will be capable of surviving, growing, and differentiating to form a healthy tissue filling the void created by the diseased tissue or the removal of a disc tissue without causing any significant undesirable compression against any nerve root or other tissue structures in or near the implantation area. Typically, the cell density in the implantation carrier can be from about $10^3$ to about $10^8$ cells/mm$^3$, preferably from about $10^4$ to about $10^7$ cells/mm$^3$ and more preferably about $10^5$ to about $10^6$ cells/mm$^3$.

The implanted intervertebral disc cells are capable of surviving, growing, and differentiating to form healthy disc tissues. As a result, the damaged disc tissue is replaced with a healthy disc tissue, and the disc disease is treated.

In the method of this invention, a small autologous healthy disc tissue from a patient needing treatment can be used to prepare healthy disc cells by in vitro cell culture. The disc cells can be re-implanted back to the diseased area in the patient. Because a large amount of healthy disc cells can be obtained with the in vitro cell culture methods, the surgical repair is not limited by the source of healthy disc cells and a sufficient number of healthy disc cells can be implanted to effectively attain the treatment objectives.

EXAMPLE 1

This example illustrates the growth of healthy disc cultures. Healthy disc tissue was obtained and rinsed with phosphate buffered saline at pH 7.4. The tissue was placed in modified Minimal Essential Medium (MEM) with Earle's salts (MEM, Gilco, Grand Island, N.Y.) with 1% (v/v) L-glutamine (Irvine Scientific, Santa Ana, Calif.), 1% (v/v) penicillin-streptomycin (Irvine Scientific, Santa Ana, Calif.), but without added serum. The disc tissue was incubated in three 15-minute rinses of MEM with 1% fungizone (Irvine Scientific) as a precaution against contamination of the cells during removal.

Regions of annulus and nucleus were visually identified and representative pieces of annulus and nucleus were dissected. Cartilaginous and vascular regions removed from tissue designated for culturing. The disc tissue to be cultured was minced with a scalpel into 1-2 mm square pieces, again rinsed twice with saline to remove clots or residual debris, placed into 35 mm culture dishes and anchored by placement of a sterile nylon mesh (Spectra Mesh, Spectra Laboratory Products) over the minced explant to provide a substrate for cell outgrowth.

A series of cultures were fed with varying amounts of cell stimulant. Minimal Essential Medium (MEM, Gibco) with Earle's salts and about 20% (v/v) of fetal bovine serum (FBS, Gibco, Grand Island, N.Y.) was added to the minced explant. The primary cultures were grown at a temperature of 37° C. and 95% humidity under a blanket of 5% $CO_2$. The primary cultures are fed with fetal bovine serum every two days.

Figure 2A:
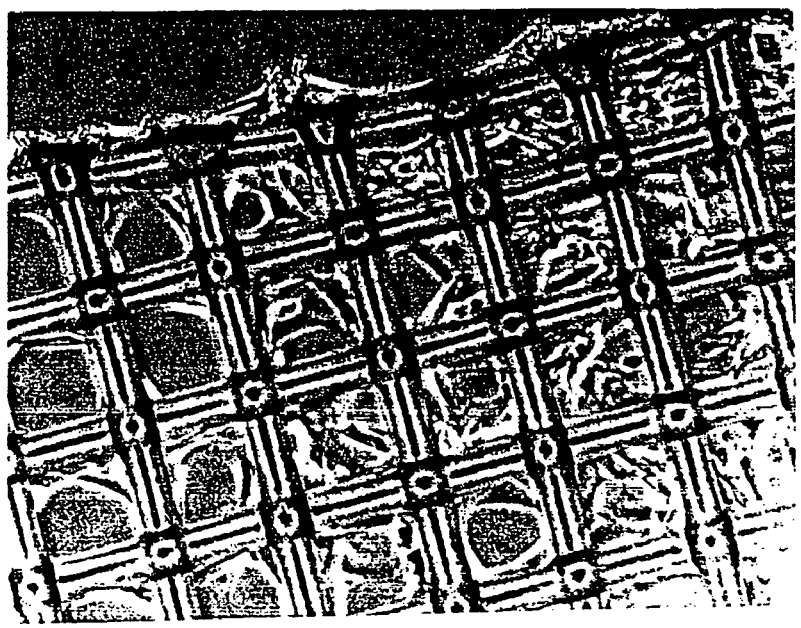
FIG. 2A is a phase-contrast photomicrograph of cells growing from a disc explant fragment onto a nylon mesh (X130)
Figure 2B:
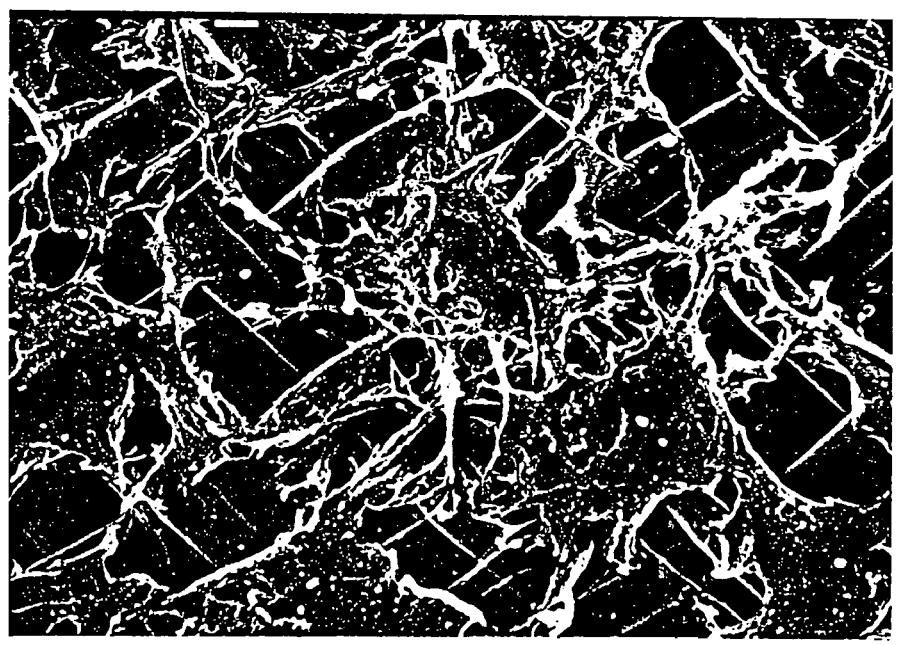
FIG. 2B is a scanning electron micrograph of cells spreading and extending processes onto the mesh (bar at the upper left, 10 µm)

Disc cells from both the annulus and nucleus grew well on the mesh lattice. Cells from the disc grew slowly even in the presence of high (20%) FBS. Cells usually required up to a month from initiation of explants until P1 cultures could be established. Doubling time in the presence of 10% FBS was 6.2 days; in 20% FBS, 3.4 days, and in 25% FBS, 3.5 days. Cell viability, determined by trypan blue exclusion, averaged 96% on monolayer culture. A phase-contrast photomicrograph of cells growing out from a disc explant fragment onto a nylon mesh (X130) is shown in FIG. 2A. In FIG. 2B there is shown a scanning electron micrograph of cells spreading and extending processes onto the mesh.

When primary cultures showed a confluent outgrowth of cells from the nylon mesh, cultures were trypsinized (1:250, trypsin (0.5 g/l), EDTA (0.2 g/l))(Irvine Scientific, Santa Ana, Calif.) and a split ratio of 1:4 used for further culturing.

EXAMPLE 2

In this example, primary cell cultures were grown in alginate. Cells established in monolayer primary culture were seeded either into alginate layers on inserts (P1 cultures) or continued as monolayer P1 cultures which were subsequently split and used as the cell source for sequential P2, P3 or P4 passages seeded into alginate. Several cryofrozen cultures were thawed and expanded as P1 passages on monolayer with subsequent P2 and later passages seeded into alginate.

The alginate solution was prepared from a 1.2% solution of Keltone LV alginate (Kelco, San Diego, Calif.) in 0.9% physiological saline with stirring for one hour. The alginate solution was sterilized by filtering through a 0.2 μm bottle top filter fitted onto a 100 ml sterile bottle.

Trypsinized primary cell cultures were assayed for cell viability and the required volume of cell suspension centrifuged at 500 rpm for five minutes in an IEC MP4R centrifuge and the medium subsequently aspirated off. An appropriate volume of sterile 1.2% Keltone LV alginate solution was added to attain the desired cell/alginate suspension. Cells were mixed in the alginate by gentle thorough pipetting.

Costar Transwell Clear Inserts (Costar, Cambridge, Mass.) were placed in multiwell plates, and the desired amount of alginate/cell suspension was carefully added to the bottom of the insert well without formation of air bubbles. A correctly prepared insert showed a fully covered filter with a meniscus formed in the insert. For a 24 well plate 50 μL of alginate/cell suspension was added to each insert. After the alginate/cell suspension was in place, each insert was carefully lifted with sterile forceps and the desired volume of 102 mM $CaCl_2$ polymerizing solution was added to the well. This volume covered the bottom of the filter, but was not enough to allow the $CaCl_2$ solution to enter into the insert. The inserts were incubated in $CaCl_2$ polymerizing solution for four minutes and the solution aspirated out. Wells were rinsed with MEM with 20% FBS (2.5 mL/well for 24 well plates).

The rinsing volume filled both well and insert, was allowed to stand for one minute, and was aspirated off. Four inserts were set up for each concentration at each time point (Days 6, 8 and 10). Each well was fed with MEM supplemented with TGF-β1)(Sigma) at the following doses: control (no TGF-β1), 0.25, 0.50, 1.0, 2.5, and 5 ng/ml. These alginate cultures were grown for ten days with feeding three times per week. Cell proliferation data, expressed as total [$^3$H]thymidine uptake/μg DNA, were obtained on days 6, 8, and 10.

The cells were removed from the alginate by rinsing the wells twice with 0.15 M $NaCl_2$ (2.5 mL/well for 24 well plates) by lifting the insert and pipetting into the well. The rinse solution was incubated for one minute, and was aspirated off via the solution under the insert. The solution within the insert was not aspirated off. After the second rinse, the remaining liquid from the insert was wicked off by gently touching a twisted sterile gauze square to the side of the tipped well. Three times the volume of the alginate in dissolving buffer (55 mM sodium citrate and 0.15 M $NaCl_2$) was added to the inside of the insert and plates incubated at 37° C. for ten minutes with shaking. Contents of the insert were gently pipetted to ensure complete dissolution of the alginate.

Figure 3A:
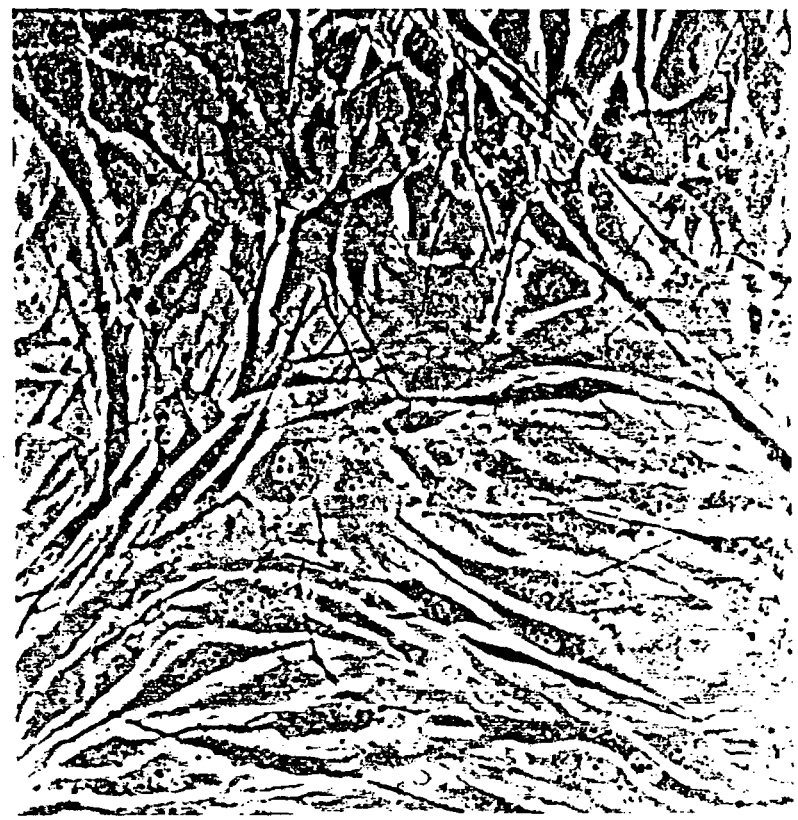
FIG. 3A shows cells grown in a three-dimensional environment.
Figure 3B:
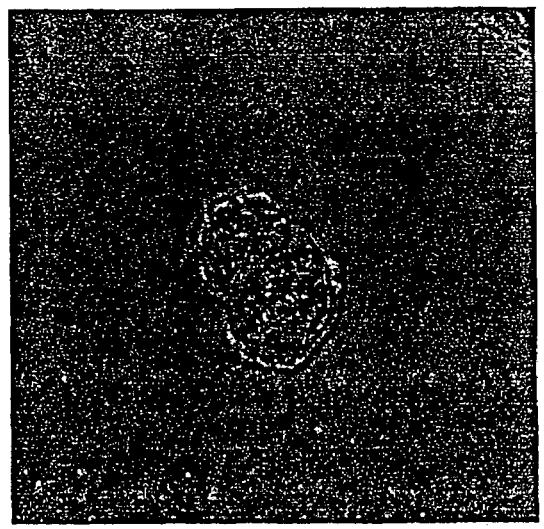
FIG. 3B is an electron microscopic examination of matrix material.

At the end of ten days, medium was withdrawn and cultures fixed with 1% neutral buffered formalin for five minutes, the insert carefully cut from the plastic holder and wrapped gently in lens paper, placed in a tissue cassette in 70% ethanol and processed using the short cycle run on a paraffin processor (Shandon Lipshaw Hypercenter XP, Pittsburgh, Pa.). Morphologic studies of cells grown in these three-dimensional microenvironments show that cells lay in a lacunar space with matrix deposited between and around the disc cells (FIG. 3A). Electron microscopic examination revealed that matrix material consisted of proteoglycans and banded and non-banded collagen (FIG. 3B). As shown in FIG. 3B, disc cells grown in the three-dimensional structure assumed a rounded morphology and formed multicelled colonies with successive cell divisions. Two colonies adjacent to each other are shown in FIG. 3B.

EXAMPLE 3

Adjacent sections of three-dimensional cultures from Example 2 cut en face were collected and utilized for immunohistochemical localization of rabbit anti-human collagen Type I or rabbit anti-human collagen Type II (Biodesign International, Kennebunk, Me.), monoclonal anti-proteoglycan delta DI-4S (ICN, Costa Mesa, Calif.) or monoclonal anti-keratin sulfate (Seikagaku Corp., Tokyo, Japan).

Figure 5A:
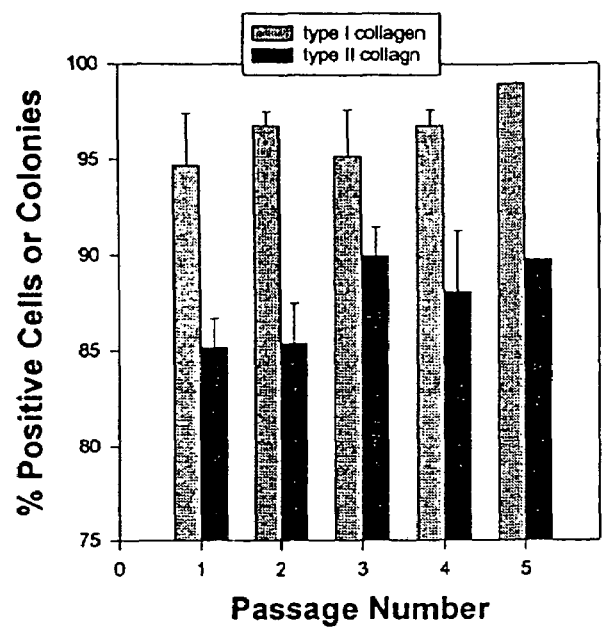
FIG. 5A presents pooled data for Type I collagen and Type II collagen.
Figure 5B:
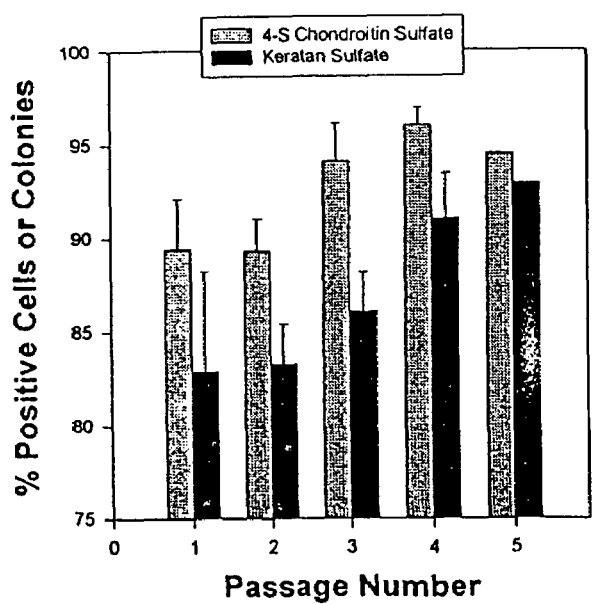
FIG. 5B presents pooled data for 4-S chondroitin sulfate and keratin sulfate.

Negative controls were incubated minus primary antibodies. Localization utilized DAB calorimetric visualization of extracellular matrix constituents. Cells or colonies were scored for positive immunohistochemical localizations using a Nikon microscope (20× objective) and OsteoMeasure computer software (OsteoMetrics, Inc., Atlanta, Ga.). The mean number of cells or colonies assessed for each localization was: Type I collagen: 272; Type II collagen: 260; proteoglycan delta DI-4S, 241, and keratin sulfate, 201. Nine surgical and two normal series of cells were studied in this experiment. Passages 1 through 4 were evaluated for cells from one specimen and one normal; passage number 3 was studies for normal; passages 1 through 3 for two specimens; passages 2 through 3 from three specimens; passages 2 through 4 in one, and passages 2 through 5 in two specimens. FIGS. 5A and 5B show the proportion of colonies positive for the presence of Type I or Type II collagen, 4-5 chondroitin sulfate or keratin sulfate.

Statistical Analysis

Data are presented as mean± SEM. SAS® (version 6.11, SAS Institute, Inc., Cary, N.C.) software was utilized for data analysis. Standard statistical methods were employed. Paired t-test were used to compare means of frozen and non-frozen matrix scoring. To detect potential bias between frozen and non-frozen groups with respect to both passage 2 and passage 3 results (examined separately), unpaired t-tests were used. A repeated measures analysis of variance was performed to test for differences over time (passages 2, 3 and 4). All tests were two-sided, and P values≦0.05 were considered statistically significant.

Figure 4:
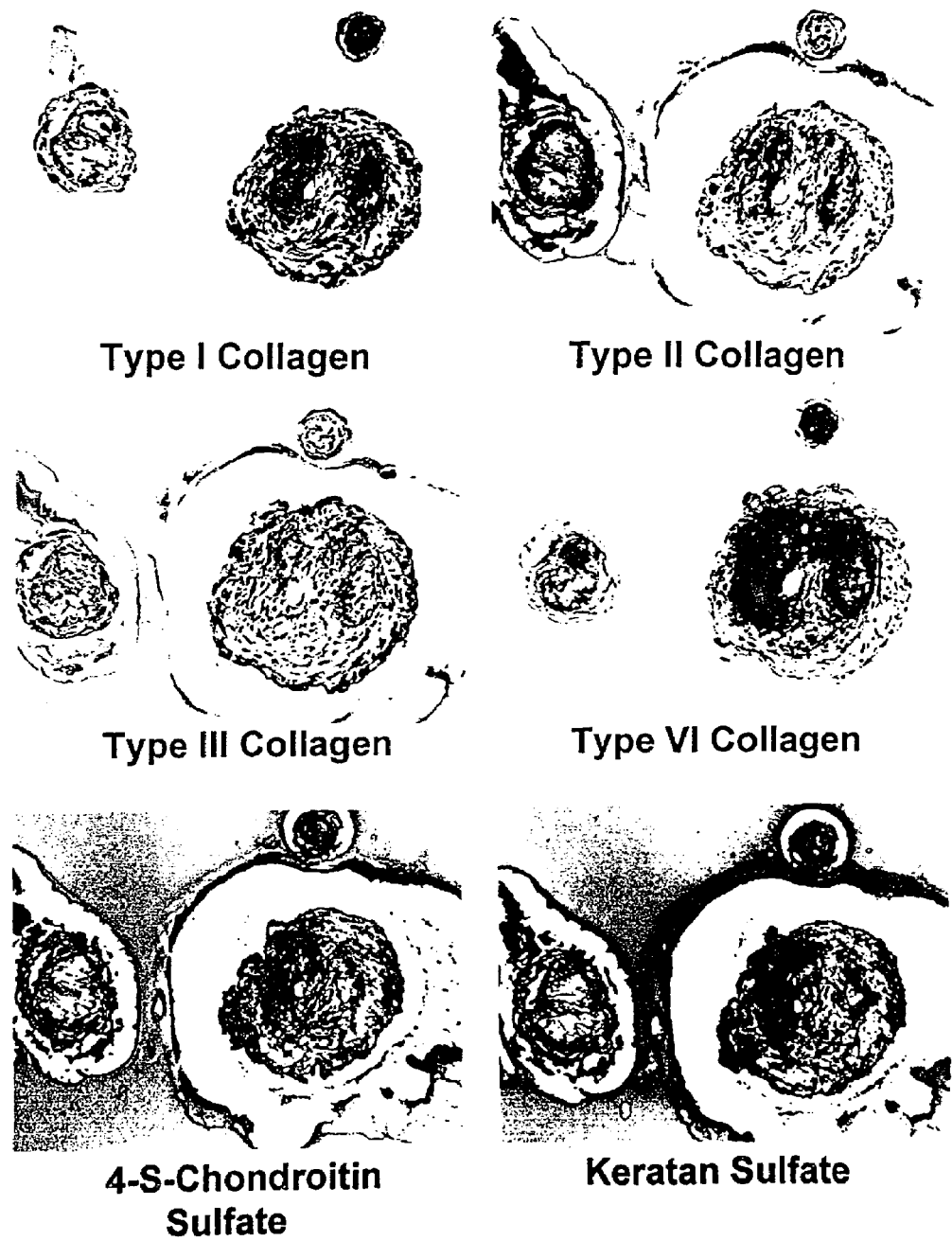
FIG. 4 is a photomicrograph of immunohistochemical localization of extracellular matrix products around first passage cells grown in agarose from a 24-year old normal subject.

Immunohistochemical Characterization of Cells Grown in Alginate and Quantitative Scoring of Matrix in Cells and Colonies Cells from the annulus were characterized using sequential passages of cells seeded into alginate over passages 1 through 5. Representative micrographs showing localization of Type I or Type II collagen or proteoglycan D1-4S or keratin sulfate are shown in FIG. 4. The micrographs illustrated in FIG. 4 show sequential serial sections with localizations of types I, II, III, and VI collagen, 4-S-chondroitin sulfate, and Keratin sulfate. Positive immunoreactivity is shown by dark staining DAB reaction product (X100).

As shown in Table 1, both non-frozen and cryo-frozen cells have been analyzed in the present study. Table 1 presents data which were analyzed by paired t-tests since the same cultures were followed through sequential passages. There were no statistically significant differences in the mean percentages of frozen and non-frozen cells with respect to the various extracellular matrix components.

TABLE 1

Summary of Quantitative Cell/Colony Scoring of Immunolocalized Extracellular Matrix Components in Non-Frozen and Frozen Cultures*

|  | Passage 1 | Passage 2** | Passage 3*** |
| --- | --- | --- | --- |
| Non-Frozen Cultures: | | | |
| Type I Collagen (n = 4) | 94.7 ± 2.7 | 96.3 ± 1.2 | 97.3 ± 1.0 |
| Type II Collagen (n = 4) | 85.3 ± 1.6 | 82.5 ± 4.0 | 86.6 ± 1.6 |
| Proteoglycan delta DI-4S (n = 4) | 89.4 ± 2.8 | 85.5 ± 1.6 | 93.8 ± 4.3 |
| Keratin sulfate (n = 4) | 82.9 ± 5.3 | 84.8 ± 2.1 | 86.0 ± 3.3 |
| Frozen Cultures: | | | |
| Type I Collagen | — | 93.3 ± 1.0 | 94.0 ± 3.8 |
| Type II Collagen | — | 87.5 ± 2.2 | 92.0 ± 2.0 |
| Proteoglycan delta DI-4S | — | 91.9 ± 2.2 | 94.4 ± 2.3 |
| Keratin sulfate | — | 82.4 ± 3.3 | 86.2 ± 2.9 |

*Data are mean % ± SEM. The total number of colonies or cells scored in each analysis ranged from 201 to 272.
**n = 6 for P2 for frozen cultures
***n = 7 for P3 for frozen cultures FIG. 5 presents pooled data for frozen and non-frozen cells studied from passages 1 through 5. These data were also evaluated using paired t-tests of passages 2 and 3 and of 2 and 4, respectively. There were no statistically significant differences between the mean of passage 2 and those of both passage 3 and 4, with respect to Type I collagen, Type II collagen and keratin sulfate. Passage 3 was found to have a significantly higher (P=0.02) mean incidence of proteoglycan D1-4S than did passage 2.

A repeated measures analysis of variance was also applied to the data in FIG. 5 which used five observations (data for all of passages 2, 3 and 4). No statistically significant changes over the course of passages 2, 3 or 4 were identified for the incidence of the four extracellular matrix components studied.

EXAMPLE 4

Figure 6:
FIG. 6A is a photomicrograph (x94) illustrating localization of engrafted cells labeled with BrdU from Example 4.
FIG. 6B is a photomicrograph (x485) showing a magnified view of a portion of FIG. 6A.

In this experiment, cells were harvested from sand rat #XFGR020, aged 9 months, from a single lumbar vertebral disc site. Cells were grown through primary explant and P1 passages (for about 3 months) at which time they were labeled in monolayer culture with BrdU ($10^{-4}$ mol/l), rinsed in buffer, trypsinized, centrifuged, resuspended in 9 μl buffer, and inserted into a 2×2 mm section of Gelfoam® (Gelfoam Sterile Sponge, an absorbable gelatin sterile sponge, Pharmacia & Upjohn) presoaked in Minimal Essential Media. 4,000 cells were seeded onto the Gelfoam. A second lumbar disc site was surgically opened, and disc material was gently extracted to make a cavity. The site showed the following radiologic signs of early degeneration: moderate wedging, moderate narrowing of the disc space, irregular disc margins and endplate calcification. Gelfoam with cells loaded therein was placed inside the cavity. The animal was euthanized after about 33 weeks and examined. Autologous cells were engrafted into the donor animal at a disc site. FIGS. 6A, 6B, 7A, and 7B show photomicrographs of the disc into which cells were engrafted and the cartilage endplates of the two adjacent vertebral bodies. Note the black-staining cells which are positive for BrdU immunocytochemical localization. This staining marks autologous disc cells which were engrafted back into the donor animals. In FIG. 6A, a low magnification view shows the central portion of the disc and to the right and left are seen the vertebral end plates of adjacent vertebrae. Arrows mark the BrdU positive cells which were engrafted or which are descendents of engrafted cells. These cells in the central region are seen to lie in large lacunae (FIG. 6B).

Figure 7:
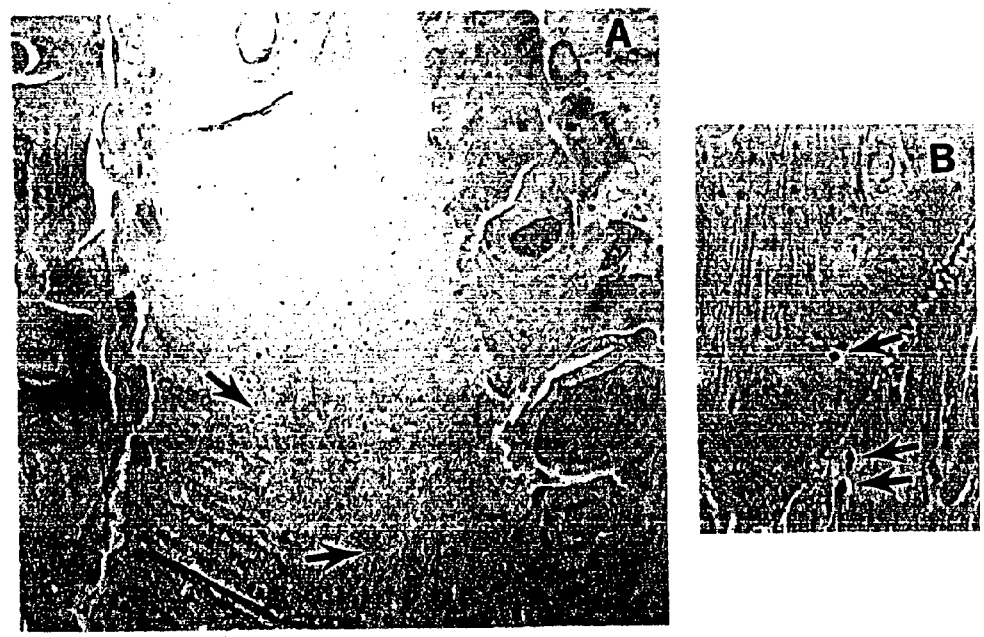
FIGS. 7A and 7B are additional photomicrographs from the specimen described in Example 4 taken from a deeper level of the tissue (FIG. 7A, X94.

Engrafted BrdU-stained cells were seen to exhibit both a chondrocyte-like phenotype in the central region of the disc (FIG. 6B) or a more spindle-shaped morphology in the outer regions of the annulus (FIG. 7B).

EXAMPLE 5

Figure 8:
FIG. 8 is a radiograph of the sand rat spine described in Example 5, which was obtained at time of euthanization.

Another 9-month old sand rat was used in an experiment similar to that described in Experiment 4. Cells from the first disc surgery were expanded for 6 weeks in primary culture, labeled with BrdU, placed in Gelfoam®, and engrafted to a different lumbar disc site. The engraftment site was marked with a vascular clamp at time of surgical closure. The animal was euthanized 33 weeks after the re-implantation surgery. FIG. 8 shows the radiologic features at time of euthanization 33 weeks after re-implantation of cells. The disc into which cells were engrafted lies just above the oval metal vascular clamp. Moderate disc wedging and some subchondral sclerosis in the vertebrae are apparent; otherwise, this procedure is well-tolerated in a healthy animal. The first disc surgery site, from which tissue was harvested for growth of cells, lies to the left of oval vascular clamp. The disc site into which cells were engrafted lied directly above the surgical clamp.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for implanting human intervertebral disc cells into a human patient with damaged or diseased intervertebral disc cells, comprising:

propagating human intervertebral disc cells in a carrier material selected from the group consisting of alginate, agarose, collagen, and mixtures thereof; and implanting said propagated human intervertebral disc cells into a target disc area needing treatment in said human patient.

2. The method of claim 1, wherein said propagated human intervertebral disc cells are provided by a process that includes the steps of:

a) obtaining a healthy human intervertebral disc tissue;

b) mincing said human intervertebral disc tissue to obtain a minced explant comprising human intervertebral disc cells; and c) culturing said minced explant under conditions to propagate and form a monolayer culture of human intervertebral disc cells, wherein the human intervertebral disc cells of said monolayer can be isolated and further propagated upon passaging.

3. The method of claim 2, wherein said disc tissue is obtained from said human patient to be treated.

4. The method of claim 2, wherein said explant is cultured in the presence of a material selected from the group consisting of transforming-growth factor beta (TGF-β), insulin-like growth factor I, insulin-like growth factor II, basic fibroblast growth factor, acidic fibroblast growth factor, platelet-derived growth factor, insulin, human recombinant bone morphogenetic protein 2, and vitamin D.

5. The method of claim 1, wherein the in vitro propagated human intervertebral disc cells are provided by a process that includes the steps of:

a) providing human intervertebral disc tissue to obtain a minced explant comprising human intervertebral disc cells;

b) culturing said minced explant under conditions to propagate and form a monolayer of human intervertebral disc cells, wherein the human intervertebral disc cells of said monolayer can be isolated and further propagated upon passaging;

c) isolating said human intervertebral disc cells from said monolayer;

d) seeding the isolated cells in said carrier material such that the isolated cells are dispersed and distributed in the carrier material forming a three-dimensional structure; and e) culturing said dispersed and distributed cells in the three-dimensional structure.

6. The method of claim 5, wherein said disc tissue is obtained from said human patient to be treated.

7. The method of claim 5, wherein said three-dimensional structure is implanted into the target disc area.

8. The method of claim 5, wherein at least a portion of said in vitro propagated human intervertebral disc cells have re-expressed extracellular matrix materials.

9. The method of claim 5, wherein said implanting step comprises:

debriding diseased or injured disc tissue in said patient; and delivering said in vitro propagated human intervertebral disc cells into the area of debridement.

* * * * *